US008216414B2

(12) United States Patent
Hornung et al.

(10) Patent No.: US 8,216,414 B2
(45) Date of Patent: Jul. 10, 2012

(54) METHOD OF PRODUCING A MULTIPLICITY OF INCONTINENCE PADS HAVING MAIN PART AND FRONT AND REAR SIDE PARTS ATTACHED THERETO

(75) Inventors: Fridmann Hornung, Lauchheim (DE); Ruediger Kesselmeier, Herbrechtingen (DE)

(73) Assignee: Paul Hartman AG, Heidenheim (DE)

( * ) Notice: Subject to any disclaimer, the term of this patent is extended or adjusted under 35 U.S.C. 154(b) by 447 days.

(21) Appl. No.: 11/992,583

(22) PCT Filed: May 30, 2006

(86) PCT No.: PCT/EP2006/005125
§ 371 (c)(1),
(2), (4) Date: Mar. 26, 2008

(87) PCT Pub. No.: WO2007/042084
PCT Pub. Date: Apr. 19, 2007

(65) Prior Publication Data
US 2009/0084497 A1 Apr. 2, 2009

(30) Foreign Application Priority Data
Oct. 12, 2005 (DE) .......................... 10 2005 048 868

(51) Int. Cl.
*B32B 37/02* (2006.01)
*B32B 38/00* (2006.01)
*B32B 38/04* (2006.01)

(52) U.S. Cl. .......................... 156/259; 156/250; 156/252

(58) Field of Classification Search .................. 156/250, 156/252, 256, 259, 263, 264, 265; 604/385.04, 604/385.21, 385.24, 367, 385.01
See application file for complete search history.

(56) References Cited

U.S. PATENT DOCUMENTS

| 4,338,938 | A | * | 7/1982 | Seavitt | 604/377 |
|---|---|---|---|---|---|
| 5,705,013 | A | * | 1/1998 | Nease et al. | 156/260 |
| 5,725,518 | A | * | 3/1998 | Coates | 604/391 |
| 5,846,232 | A |  | 12/1998 | Serbiak |  |
| 6,193,701 | B1 |  | 2/2001 | Van Gompel |  |
| 6,264,643 | B1 | * | 7/2001 | Toyoda | 604/385.29 |
| 6,319,347 | B1 | * | 11/2001 | Rajala et al. | 156/164 |
| 2004/0172002 | A1 | * | 9/2004 | Nelson et al. | 604/385.02 |
| 2005/0256495 | A1 |  | 11/2005 | Schlinz |  |
| 2007/0142808 | A1 | * | 6/2007 | Wada et al. | 604/385.3 |
| 2008/0210067 | A1 |  | 9/2008 | Schlinz |  |

FOREIGN PATENT DOCUMENTS

| EP | 0 573 586 | | 12/1993 |
|---|---|---|---|
| EP | 0 650 714 | | 5/1995 |
| EP | 0 923 920 | | 6/1999 |
| EP | 1 260 203 | | 11/2002 |
| EP | 1 415 628 | | 5/2004 |
| EP | 1 428 487 | | 6/2004 |
| EP | 1 574 191 | | 9/2005 |
| EP | 1731122 A1 | * | 12/2006 |
| JP | 04-261655 | | 9/1992 |
| JP | 09-503692 | | 4/1997 |
| JP | 2000-500684 | | 1/2000 |
| JP | 2001-129016 | | 5/2001 |
| JP | 2002-532195 | | 10/2002 |

* cited by examiner

*Primary Examiner* — Mark A Osele
*Assistant Examiner* — Christopher C Caillouet
(74) *Attorney, Agent, or Firm* — Paul Vincent

(57) ABSTRACT

Method of producing an incontinence pad having a main part and front and rear side parts attached thereto, characterized in that the rear side parts can be expanded to a greater extent than the front side parts.

22 Claims, 12 Drawing Sheets

METHOD OF PRODUCING A MULTIPLICITY OF INCONTINENCE PADS HAVING MAIN PART AND FRONT AND REAR SIDE PARTS ATTACHED THERETO

This application is the national stage of PCT/EP2006/005125 filed on May 30, 2006 and Paris Convention Priority to DE 10 2005 048 868.4 filed Oct. 12, 2005.

BACKGROUND OF THE INVENTION

The invention concerns a method for producing a multiplicity of disposable incontinence pads having a pad main part and front and rear pad side parts attached thereto.

The attached side parts of disposable incontinence pads, i.e. hygiene articles that are normally used for adults, in particular for older people, usually protrude. They are used for correct positioning of the hygiene article on the body and may also be designed to be elastic or elasticised.

It is the underlying purpose of the present invention to provide an inexpensive method for producing such disposable incontinence pads, which can be advantageously realized with respect to the technical process.

SUMMARY OF THE INVENTION

This object is achieved in accordance with the invention by a method comprising the following steps:
  supplying and feeding an endless pad main part sheet in a first longitudinal direction to an application station,
  supplying an endless pad side part sheet to be provided with expandable areas,
  separating the longitudinal sections of the pad side part sheet, supplying the longitudinal sections to the application station, and positioning them on the main part sheet of the pad,
  undetachably fixing the longitudinal sections of the pad side part sheet to first areas of the pad main part sheet, wherein each first area comprises a front hip area and a rear hip area of two abutting pad main parts that border each other in the longitudinal direction,
  singling the disposable incontinence pads by separating the pad main part sheet transversely with respect to the longitudinal direction, wherein separation is effected through the longitudinal sections in such a fashion that a first partial section of a respective longitudinal section forms a front pad side part of a first disposable incontinence pad and a second partial section of the respective longitudinal section forms a rear pad side part of a directly bordering second disposable incontinence pad, wherein the rear pad side part has a higher expansibility than the front pad side part.

Expansion defines the ratio between an increase in length of a pad side part due to the action of a force and the original length. Forces act on the pad side parts, in particular, in the peripheral direction, i.e. transversely to the pad, during use of such disposable incontinence pads. The property "expansibility" thus defines the degree of expansion of the pad side part in response to a force that acts in the transverse direction of the pad. This means, the higher the degree of expansion the higher the expansibility. In accordance with the invention, a rear pad side part expands more than a front pad side part under the action of normal forces during use of the pad. In particular, in accordance with a test method to be described below, a rear pad side part expands more than a front pad side part under the action of a force of 45 N. A rear pad side part preferably expands by at least 20%, in particular at least 25%, and moreover in particular at least 30% under the action of a force of 45 N. In contrast thereto, a front pad side part expands only by preferably at most 15%, in particular at most 10%, and moreover at most 8%, under the action of a force of 45 N.

At least one rear pad side part is advantageously elastically expandable at least in a transverse direction. The expansibility of the pad side part is termed elastic when a temporarily exerted force produces an expansion of at least 40% of which at most 20% remains (remaining expansion) when this force is eliminated.

In an advantageous further development of the invention, the elastic expansibility of a rear pad side part in the transverse direction is at least 40%, in particular at least 50%. According to a further inventive idea, the absolute extent of the elastic extension of a rear pad side part is at least 3 cm, in particular at least 5 cm, and moreover at least 7 cm.

In accordance with the inventive method, a pad main part sheet is supplied in an endless fashion, and pad side parts are joined to this pad main part sheet in a manner as claimed above. The pad side parts originate from an endlessly supplied pad side part sheet from which longitudinal sections are separated, applied to the endlessly supplied pad main part sheet, and fixed thereto. In accordance with the invention, a separating cut is performed through a respective longitudinal section for singling the disposable incontinence pads, such that one partial section of this longitudinal section belongs to one incontinence article and the other partial section belongs to the neighboring incontinence article. In an advantageous fashion, the relevant areas of the pad side part sheet are designed as mentioned above in view of their expansibility, the above-mentioned longitudinal sections are separated from the pad side part sheet, and the separating cut during singling of the disposable incontinence articles is guided in such a fashion that a rear pad side part, i.e. a pad side part which is joined to the rear hip area or rear area of the pad main part has a higher expansibility than a front pad side part which is joined to a front hip area or belly area of the pad main part. It has turned out that this differentiated expansibility improves the fit of the incontinence article or in other words, there is no need to provide mutually corresponding expansibilities in the front and rear pad side parts. Since the provision of expansibility properties, in particular elastic expansibility properties, always involves costs, the realization of differentiated expansibilities of the front and rear pad side parts is advantageous for this reason alone. This requires, however, provision of a varied expansibility of the pad side part sheet. This can be realized in many ways, preferably prior to but also after application of the longitudinal sections of the pad side part sheet to the pad main part sheet, which is described in more detail below with reference to the embodiments.

The pad main part or the pad main part sheet may basically be produced in a continuous fashion in the longitudinal direction, in particular, from non-woven or foil material or from a non-woven/foil composite material. In another advantageous fashion, a respective pad main part has an absorption core comprising liquid-storing, preferably super-absorbent materials, which can be disposed, in particular, as a pre-fabricated unit onto a carrier sheet of the pad main part sheet. This carrier sheet could e.g. comprise a foil layer or also a composite foil with a thin non-woven support on the later outer side, wherein absorption cores can be disposed onto this carrier sheet one after the other in the longitudinal direction and at a separation from each other, and preferably be fixed to the carrier sheet. This may be a pre-fabricated absorption core, as mentioned above, which is also often called suction element, or the absorption core may be constructively formed by disposing absorbent fiber material, preferably with super-absorbent polymer materials.

In another advantageous fashion, first elastic elements that extend in the first longitudinal direction are joined to both sides of the pad main part sheet. These elastic elements may also be provided along the leg openings following a defined contour, or may also extend exactly in the longitudinal direction.

Moreover, second elastic elements that extend in the first longitudinal direction, in particular, in the form of so-called upright cuff elements which are disclosed per se e.g. in EP0263720A1, may be attached to the pad main part sheet. These preferably upright second elastic elements quasi flank a center of the pad main part or of the suction element. They may be provided in the area of the suction element edges, within the suction element edges or outside of the suction element edges. They form a lateral outlet protection of the incontinence article.

In accordance with an advantageous variant of the inventive method, the longitudinal sections are supplied to the application station with a first speed v1 and the endless pad main part sheet is supplied to the application station with a second speed v2, wherein the first speed v1 is slower than the second speed v2. In this case, the longitudinal sections of the pad side part sheet are separated at a relatively low speed v1 and then preferably accelerated to the speed v2, such that the longitudinal sections are preferably disposed onto the pad main part sheet at the same speed v2. This acceleration may e.g. be performed by an application roller which can be pressurized, in particular, by under pressure, and is disposed in the transporting direction of the pad side part sheet of a separating or cutting station where the longitudinal sections are separated, in particular, directly thereafter.

In a preferred embodiment of the invention, the second speed may be faster than the first speed v1 by at least 40%, in particular at least 70%, in particular at least 90%, in particular at most 200%.

In accordance with a further particularly important embodiment, the pad side part sheet may comprise a first carrier material which has a regular pattern, in particular, of window-like recesses, which are bridged by elastically expandable material or elastic elements such as e.g. elastic foils or elastic non-woven materials. By introducing recesses into the carrier material, which are bridged by elastic material in the broadest sense, one can produce an expansibility that differs from that of the carrier material. If e.g. the carrier material is substantially non-expandable, little expandable or at least less expandable than the pad side part to be produced, the carrier material that is modified in the above-described fashion with openings bridged by elastic material has a larger expansibility than the original carrier material.

The above-mentioned recesses may be provided in the carrier material of the pad side part sheet already prior to entry into the production machine, or they are advantageously cut or punched out only directly during production of the inventive disposable incontinence pads in the pad production machine. The latter is advantageous in that the carrier material can be introduced into the production machine in an endless fashion from the roll without previous positioning, which also facilitates roll change. The elastic material or the elastic elements can also be disposed in the carrier material of the pad side part sheet via the recesses in the carrier material already prior to entry into the production machine and be fixed with respect to the carrier material, or they are advantageously disposed only directly during production of the inventive disposable incontinence pads within the machine via the recesses in the carrier material and fixed with respect to the carrier material.

The recesses are introduced into the carrier material and the longitudinal sections are separated from the pad side part sheet in such a fashion that the recesses are advantageously disposed only within the second partial sections. A respective first partial section thus remains substantially unchanged with respect to expansibility properties of the first carrier material. The respective second partial section, however, is expandable due to the elastic material that bridges the recess. Elastic expansibility is provided by applying elastic material or elastic elements.

The provision of recesses in the pad side part sheet enables working with a continuous carrier material that is endless in the longitudinal direction and has recesses in correspondence with the position of the longitudinal sections to be separated and with the position of the partial sections of these longitudinal sections, which are bridged by elastic material. It is thus possible to realize differentiated expansibility of a sheet which is continuous in the longitudinal direction.

One further possibility to obtain modification of the expansibility properties in some areas consists in weakening again some areas of the pad side part sheet in an alternating fashion, preferably by a technology known as "ring rolling" technology. This technology is described e.g. in EP 0 573 586 B1 and EP 0 650 714 A1. By "ring rolling", a material which is not expandable per se, e.g. a foil material or a non-woven/foil laminate, is overstretched by excessive deflection between intermeshing rollers. In this overstretched state, the material which is not expandable per se does not substantially resist elongation. Elastic expansibility in the correspondingly treated area can thus be achieved through combination with an elastically expandable element. It is therefore advantageous to form the elastic areas of the pad side part sheet by applying elastic material onto the carrier material and overstretching the carrier material in some areas.

The elastically expandable material which can be provided for the pad side part sheet could be disposed in an alternating fashion in the longitudinal direction, i.e. at a separation from each other on the pad side part sheet. It may also be advantageous to form the elastic elements of the pad side part sheet by a material that extends continuously in the longitudinal direction of the pad side part sheet, in particular, a lamellar elastic material which is activated only in sections in the longitudinal direction. This sectional activation can be realized by local weakening of the carrier material, e.g. by providing recesses or by "ring rolling" or in any other fashion e.g. also by providing perforations, as mentioned above. Although the arrangement of an elastic material that is continuous in the longitudinal direction involves corresponding material costs, this arrangement turns out to be easier in terms of construction for fast-running machines than intermittent disposal of elastic material.

In another advantageous further development of the invention, at least two, preferably exactly two, expandable preferably elastically expandable areas are provided in the second partial section of the pad side part sheet. In a particularly advantageous fashion, a first expandable area is provided on or in the vicinity of the upper transverse edge of the second partial section and a second expandable area is provided on or in the vicinity of the lower transverse edge of the second partial section. In this case, the rear pad side part has a greater expansibility at exactly that position where, according to experience, the highest forces act during use, e.g. during closing the disposable incontinence pad. Tearing off the pad side parts from the main part can thereby be prevented.

The elastic material or elastic material sections could be provided on an upper side or lower side of the carrier material of the pad side part sheet. It has turned out to be advantageous to dispose the elastic material like a sandwich between a first and a second carrier material of the pad side part sheet.

The pad side part sheet or the above-mentioned longitudinal section of the pad side part sheet could be separated in the longitudinal direction into a left-hand and a right-hand part prior to application, which are then applied and fixed to the left-hand or right-hand side edge of the pad main part sheet. In accordance with another embodiment, a longitudinal section of the pad side part sheet could be designed continuously in one piece in a transverse direction of the pad, such that it continuously bridges the respective front or rear hip area of the pad main part.

The disposable incontinence pad is finally singled after application and fixing of the partial sections of the pad side part sheet to the pad main part sheet. Towards this end, substantially one single separating cut may be guided through the longitudinal section and the pad main part sheet. It is also feasible to guide the separating cut only through the longitudinal section, i.e. if the pad main part sheet has been previously separated transversely to the longitudinal direction for forming individual pad main parts, which are then fed, at a certain separation from each other, to the application station where the longitudinal section covers this separation like a bridge. Common singling, wherein the cut extends through the longitudinal section of the pad side part sheet and also through the pad main part sheet is, however, preferred.

Instead of the design of one single separating cut that extends transversely to the longitudinal direction, it may be advantageous for singling the disposable incontinence pads or for separating the longitudinal sections to form a section to be discarded. This would be feasible e.g. through two so-called contour cuts or one e.g. rectangular (punching) cut, wherein the sheet is separated and a rectangular section is formed which is to be discarded. In this fashion, material is lost, but a certain positioning inaccuracy can be compensated for. It can thereby be ensured, in particular, that a previously (discontinuously) disposed section of elastic material is only provided in the intended second partial section and does not also extend in an undesired fashion into the first partial section due to an inaccurate separating cut. This can be prevented with the required process reliability by discarding a section to be discarded of a sufficient width in the longitudinal direction of, in particular 5 to 20, in particular 5 to 15, in particular 5 to 10 mm. When contour cuts are used that differ from the exactly linear shape, it is moreover possible to realize a contour as indicated e.g. in FIG. 8.

Irrespective thereof, in accordance with an independent inventive idea, the front pad side parts may advantageously substantially be non-expandable while the rear pad side parts are expandable, in particular elastically expandable. In a further development of this independent inventive idea, the length of the rear pad side parts, i.e. their extension in the longitudinal direction of the pad, is advantageously at least 10 cm, in particular at least 15 cm, moreover in particular at least 18 cm, and moreover, in particular at least 22 cm. Moreover, the length of the rear pad side parts is advantageously at least 10%, in particular at least 15%, in particular at least 20%, and moreover, in particular at least 22% of the overall length of the disposable incontinence pad. The overall length of the disposable incontinence pad is advantageously 50 to 120 cm, in particular 60 to 110 cm, and moreover in particular 70 to 110 cm. Moreover, the front pad side parts advantageously have a smaller longitudinal extension than the rear pad side parts, in particular by at least 5%, in particular at least 10%, in particular at least 15%, and moreover, in particular at most 50%. In a further development of the invention, the width of the pad side parts, i.e. the extension of the pad side part past the side edge of the pad main part is advantageously 10 to 40 cm, in particular 12 to 30 cm, in particular 13 to 25 cm. The front pad side part advantageously has the same width as the rear pad side part.

The pad side parts joined to the pad main part are advantageously formed from a non-woven material, at least in some areas. In particular, spunbond materials (S) or spunbond-meltblown materials (SM), or meltblown layers (SMS), which are provided on both sides with spunbond materials, or also carded non-woven materials are preferably used. Non-woven laminates, i.e. in particular, two-layered, three-layered or multi-layered combinations of the above-mentioned non-woven materials may also be used. The individual layers may e.g. be connected by conventional and familiar methods, e.g. through thermal joining methods (welding, in particular laser welding, hot melt, air-through) or through ultrasound welding methods. Cold pressing, needling, sewing or gluing of non-woven materials is also feasible. Connection to textile tissues, knitted fabrics, i.e. to materials having a textile bond in the broadest sense as well as foils and foam materials is also feasible. The pad side parts joined to the sides of the pad main part are designed to be breathable at least in sections, wherein, in particular, porosity is regarded as being advantageous which permits air exchange and also permeability for moisture in the form of water vapor. The pad side part material advantageously has a surface density of 10 to 150 g/m$^2$, in particular 20 to 100 g/m$^2$ and preferentially 25 to 50 g/m$^2$.

In another advantageous fashion, the pad side parts are folded on top of themselves and/or onto the pad main part about at least one folding line that extends in the first longitudinal direction. In a further development of this idea, the folded pad side parts are advantageously detachably fixed to joining locations or joining areas, as disclosed in DE202004006951.2, the entire disclosure of which is hereby incorporated by reference, in particular, by ultrasound weld points. In this fashion, the relevant pad side part can be held in a controllable stable configuration in the technical process within the production machine and fluttering up can be reliably prevented.

Folding and optionally detachably fixing of the folded pad side parts is preferably performed prior to separating the longitudinal sections. The still endless pad side part sheet is thereby preferably folded, which is advantageous due to the more compact design of the subsequent application stations.

In a further development of the invention, a gripping area for unfolding the pad side part is provided at a partial area forming the free end of the pad side part in a transverse direction of each folded pad side part. In the simplest case, this gripping area may be formed by a longitudinal side edge section of the mentioned partial area which a user can grip with his/her fingers. It is also feasible to provide a separate manually graspable gripping element on the respective partial area, which would, however, involve additional production expense.

In this connection, in accordance with a particularly advantageous and preferred further development of the inventive incontinence article, the detachable fixing can advantageously be separated at all joining locations or joining areas during unfolding through pulling once a gripping area of the respective pad side parts. This further facilitates handling and the incontinence article is thereby even user-friendlier, in particular, for application to persons needing a great deal of care.

The above-mentioned complete unfolding of the folded pad side parts by pulling once a gripping area, i.e. by one single pulling motion, means that the user does not have to abruptly pull or even tear several times a respective pad side part until all joining locations between the partial areas of the pad side part and optionally also with the pad main part of the incontinence article are released.

In the simplest case, a respective pad side part is folded on top of itself about a folding line, such that two partial areas lie on top of each other or against each other. The pad side part is preferably folded on top of itself about at least two folding lines to obtain a Z-shaped cross-sectional configuration. In accordance with a further preferred embodiment, the pad side parts are folded on top of themselves about three folding lines. According to a further preferred embodiment, the pad side parts are folded on top of themselves about four folding lines.

In accordance with a further preferred embodiment of the inventive incontinence article, the respective gripping areas face the outside in a transverse direction prior to unfolding of the pad side parts, i.e. face away from each other and from a longitudinal center axis of the pad main part which is spread out on a flat support, such that a user can easily grip it with his/her left hand from the left-hand side and with his/her right hand from the right-hand side.

Detachable fixing of the partial areas of the pad side parts, which are folded on top of themselves, to each other and possibly also to the pad main part is preferably formed by several substantially dot-shaped joining locations. A dot-shaped joining location of the above-mentioned type means that the joining location has a surface (as projected on the X-Y-plane of the pad main part) of less than 5 mm$^2$, in particular less than 2 mm$^2$, and moreover, in particular, less than 1 mm$^2$. The joining locations need not be strictly dot-shaped or circular. Other shapes than dot-shaped or circular, such as triangular, rectangular, polygonal or oval shapes are also feasible and advantageous. The partial areas of the pad side parts, which are folded on top of themselves, are advantageously detachably fixed to each other through preferably dot-shaped joining locations generated by heat or ultrasound.

It has turned out in accordance with the invention that the number, distribution or surface portion of the joining locations or the adhesion of the detachably joined partial areas can be selected such that detachable fixation to all joining locations or joining areas can be released during unfolding by pulling the respective gripping area of the pad side parts once. This can be advantageously supported in that the number or the surface portion of the joining locations or the adhesion of the detachably joined partial areas decreases with decreasing distance from the gripping area of the pad side part. In accordance with the invention, it has turned out that the greater the distance between an area of partial areas of the pad side parts, which are folded on top of each other, and the gripping area, the smaller should be the strength of fixation of the partial areas to each other in order to be able to release all joining locations or areas through pulling once the respective gripping area of the pad side parts, i.e. through one single unfolding motion. It has accordingly also turned out that the partial areas which are folded on top of each other can be easily detachably fixed with varying strength in the vicinity of the gripping area in accordance with the requirements. This ensures safe transport of the flat material sheets which are already folded preferably upstream of or in the fast running pad production machine, thereby preventing pad side parts that laterally protrude from the pad main part of the incontinence article from fluttering or partial areas which are folded on top of themselves from being displaced within the fold. Folding of the overall product at a later time yields a neat appearance.

In a further development of the invention, the pad side parts are advantageously folded inwardly about a folding axis that extends in the longitudinal direction onto the side of the pad main part facing the body prior to use of the folded article, to form an arrangement which is folded on top of itself, such that a first rear pad side part, e.g. the right-hand side, rests at least in some areas below the second, e.g. the left-hand side, rear pad side part. A respective pad side part may thereby advantageously be folded on top of itself at least about a folding line that extends in the longitudinal direction as described above. This folded arrangement is preferably detachably fixed to a first joining location. Reference is thereby made to the full disclosure of DE102005035544.7, the entire disclosure of which is hereby incorporated by reference.

The pad side parts, preferably the rear pad side parts, comprise closure elements for closing the incontinence article when applied to a user, which may be mechanically adherent or adhesive and which are preferably themselves arranged in a folded configuration on the pad side parts that can be unfolded for use. The closure elements suitably cooperate with a contact area on the outer side of the pad main part and/or on the pad side parts in a detachable adhesive fashion or by glue.

Finally, the singled disposable incontinence pads are advantageously folded about at least one folding line that extends transversely to the first longitudinal direction.

The invention also concerns disposable incontinence pads comprising the features in correspondence or in accordance with the features of the attached method claims of the present patent application.

Protection is claimed, in particular, for a disposable incontinence pad with a pad main part and front and rear pad side parts which are joined thereto, wherein the rear pad side parts have a greater expansibility than the front pad side parts. Protection is also sought for a disposable incontinence pad comprising a pad main part and front and rear pad side parts joined thereto, wherein the rear pad side parts have a greater expansibility than the front pad side parts in combination with one or more of the features of the embodiments of the invention described above or below.

Further features, details and advantages of the invention can be extracted from the attached claims, the drawing and the following description of a preferred embodiment of the inventive method.

A test for determining the expansibility is described below. The expansibility of pad side parts up to a defined force limit is determined in a tension test using a tension testing device according to EN ISO 527-1 (April 1996).

Sample Preparation:

A pad side part, joined to the pad main part, of a disposable incontinence pad that was previously conditioned for 24 h at 23° C. and 50% relative air humidity, is initially separated along a side longitudinal edge of the pad main part, thereby destroying the joint. A blade or scissors can be used for this purpose. If the pad side part is detachably fixed at the joining locations or joining areas in a configuration in which the pad side parts are folded on top of themselves or folded on top of each other, all joining locations and joining areas are initially manually released prior to separation from the pad main part, and the pad side part is completely unfolded. The pad side part, centered with a longitudinal side edge, is then fixedly clamped to a lower clamp of the tension testing device over its entire length (in the longitudinal direction of the incontinence article) with which it was previously joined to the pad main part (clamping depth 15 mm). The lower clamp of the tension testing device must therefore have a corresponding length, suitably a length of 300 mm. The movable clamp of the tension testing device is also fixedly clamped along its entire length at the opposite free longitudinal side edge of the separated pad side part (clamping depth 15 mm). The initial length to be subjected to the tensile force thus corresponds to the full pad side part width minus the clamping depth in the clamps. Through controlled motion of this movable clamp, a tension test up to the defined force limit, in particular to a force of 45 N, is performed and the expansibility in % of the initial length is determined.

Test Parameters:
  clamping depth: 15 mm in each case
  test speed of the movable clamp: 300 mm/min
  measured path: expansion until the defined force value of 45 N is reached,
  pre-force: 0.2 N.

DESCRIPTION OF THE PREFERRED EMBODIMENT

Figure 1:
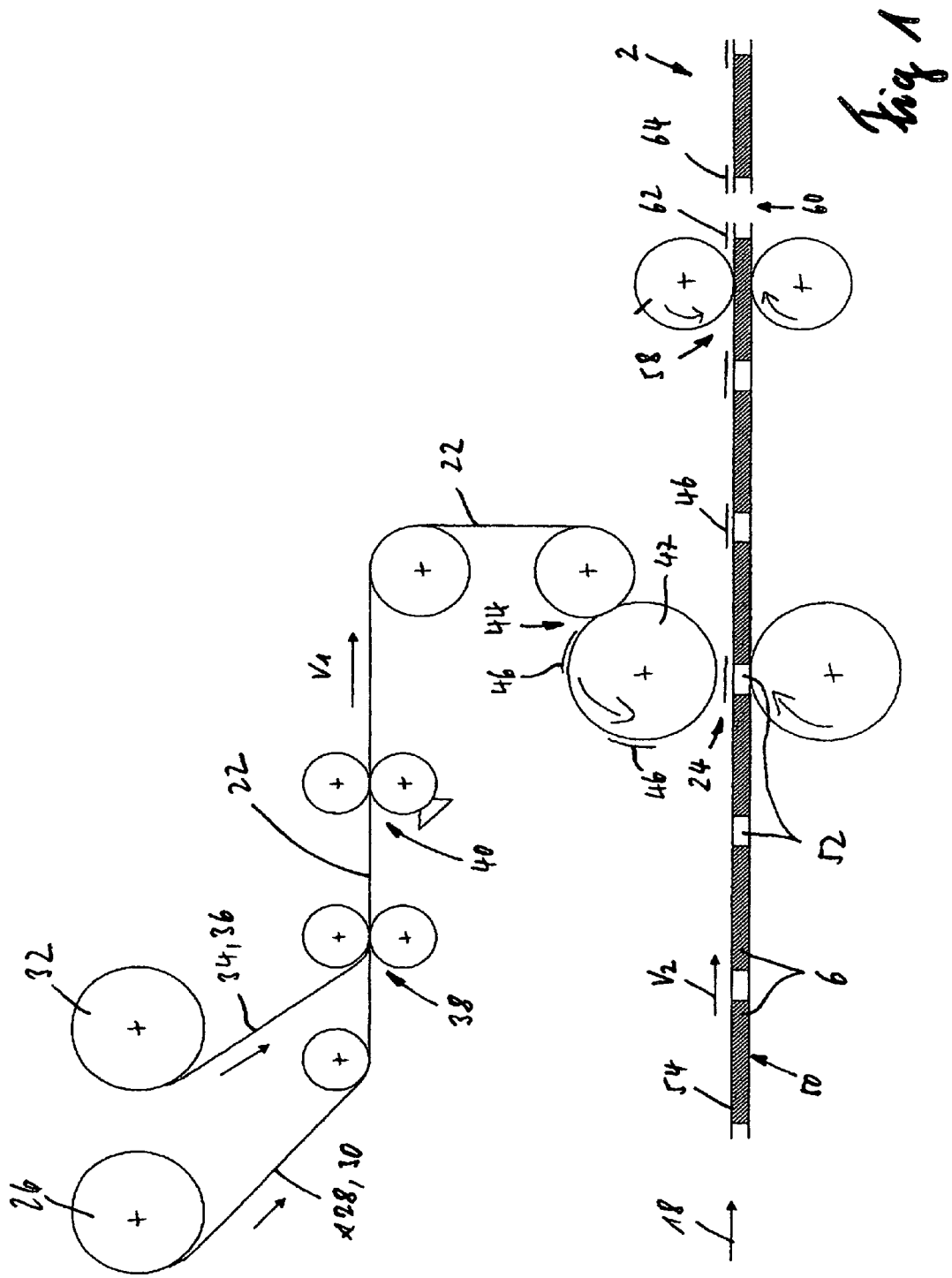
FIG. 1 shows a schematic view of the inventive production method.
Figure 2:
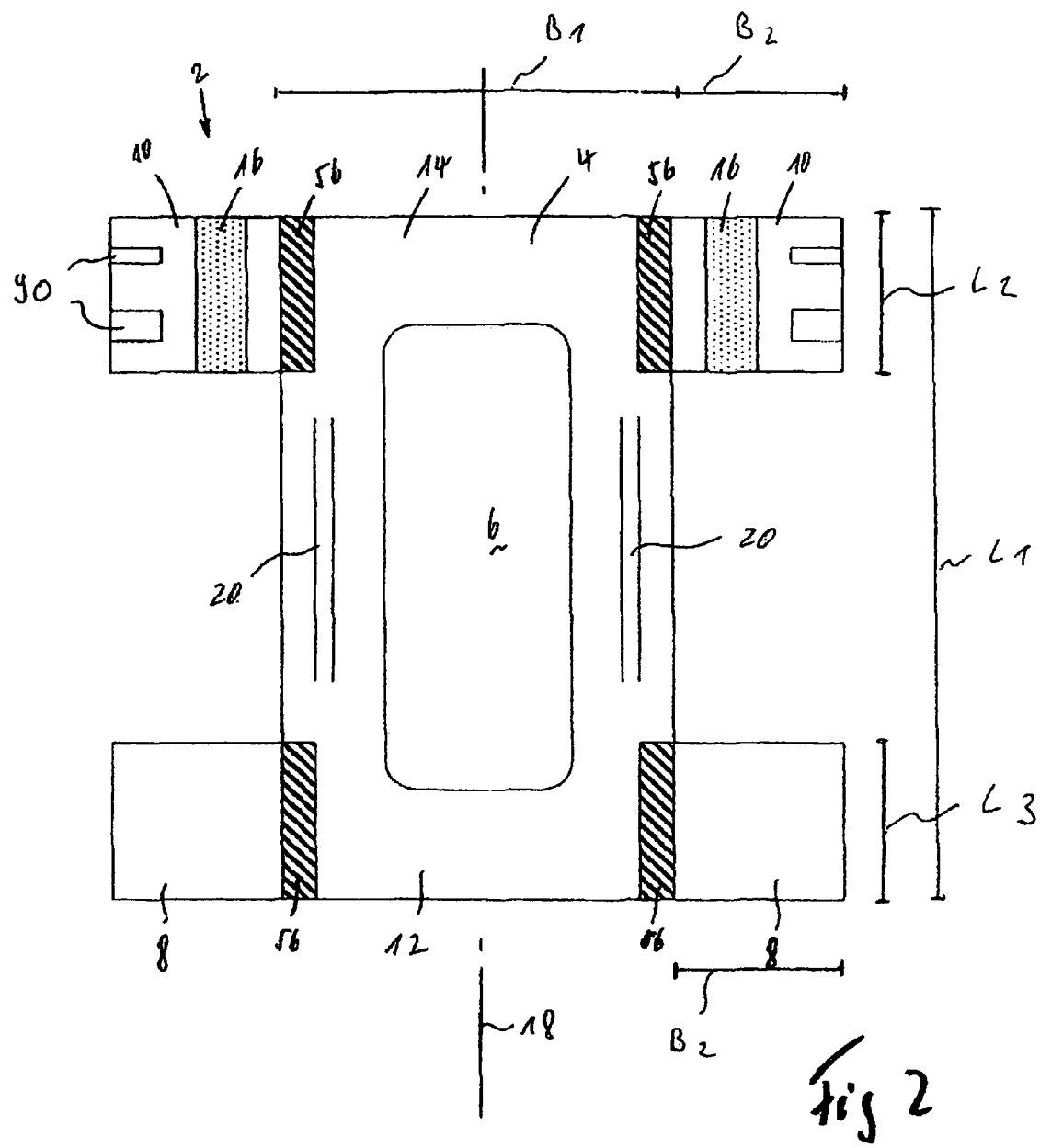
FIG. 2 shows a schematic top view of a disposable incontinence pad produced according to the inventive method.

FIG. 1 clearly shows the inventive method for producing a plurality of disposable incontinence pads 2 which are schematically shown in the top view of FIG. 2. The disposable incontinence pads 2 to be produced (called pads 2 below) comprise a pad main part 4 with an absorption core 6 disposed thereon, whose longitudinal extension is smaller than the longitudinal extension of the pad main part 4, and front pad side parts 8 and rear pad side parts 10. In the case represented in FIG. 2, the length of the pad main part L1 is 815 mm. The width B1 of the pad main part is 320 mm. The length L2 of the rear pad side parts is 230 mm. The length of the front pad side parts L3 is 170 mm. The width B2 of the front and rear pad side parts is uniformly 170 mm. The front and rear pad side parts 8 and 10 are undetachably joined to a front hip area 12 or a rear hip area 14 of the pad main part 4 (laterally in each case in FIG. 2). The rear pad side parts 10 have a greater expansibility than the front pad side parts 8, which is schematically indicated by an elastically expandable area or section 16 at the rear pad side parts 10. First elastic elements 20 are also indicated, which extend in a longitudinal direction 18 of the pad on both sides of the absorption core 6. Further second elastic elements (not shown) may be provided in the form of upright cuff or collar elements which form a lateral outlet protection substantially at the edges of the absorption core 6. Closure elements 90 are schematically indicated, which are disposed at the rear pad side parts and can cooperate in an adhesive fashion with the outer side of the pad main part and preferably also with the front pad side parts during use.

Figure 6:
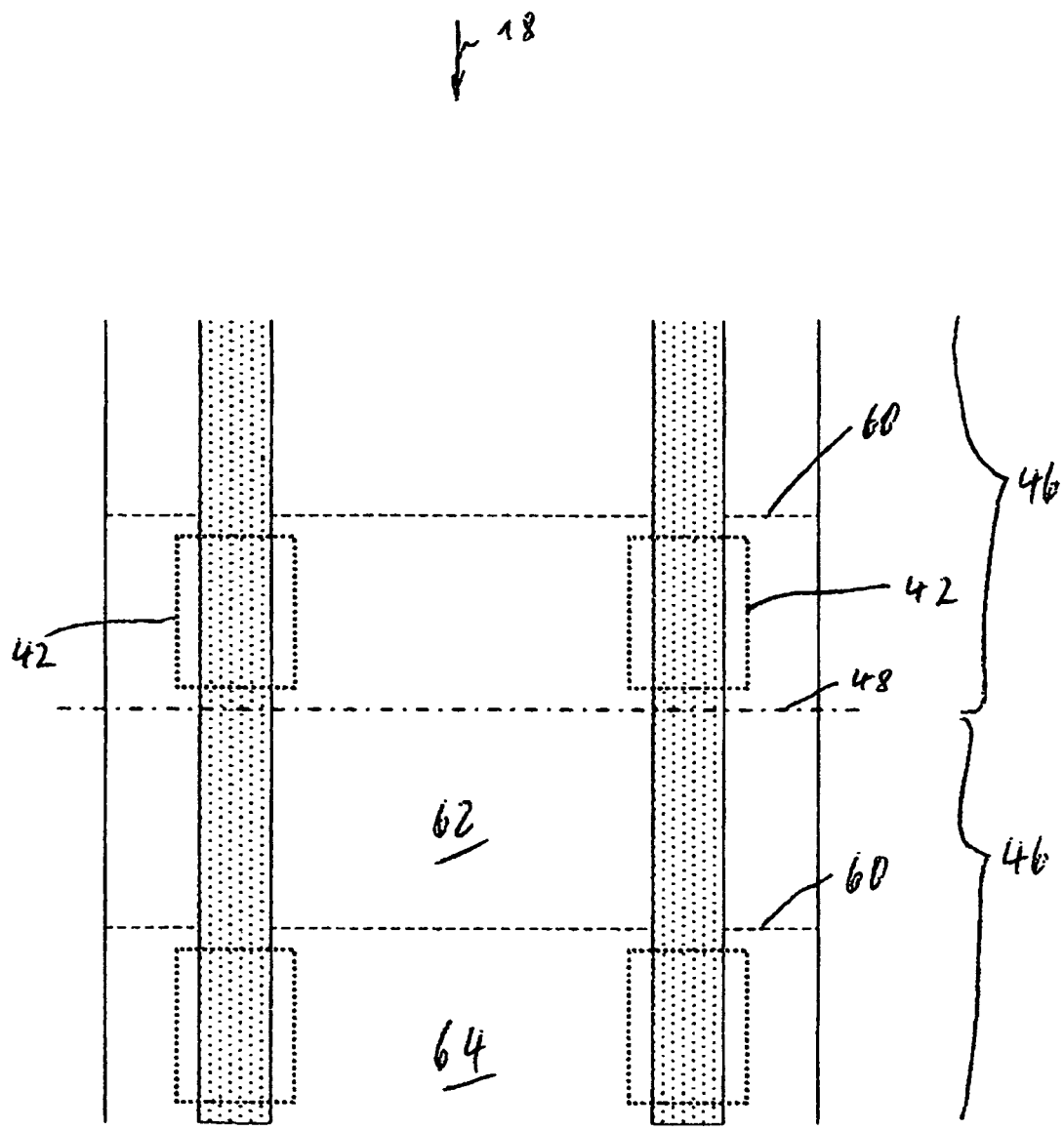
FIG. 6 shows a top view of a pad side part sheet according to a further inventive method variant with an elastic material that is continuous in the longitudinal direction.

For producing the pad 2, a pad side part sheet 22 is formed in accordance with FIG. 1 (upper area) and supplied towards an application station 24. The pad side part sheet 22 comprises a first sheet 28, which can be endlessly unrolled from a supply roll 26, of a substantially non-expandable carrier material 30, and a second sheet 34 of an elastically expandable material 36 that can be endlessly unwound from a supply roll 32. The second sheet 34, which is only schematically shown in FIG. 1, may e.g. comprise two strip-shaped sheets which are separated from each other in the transverse direction, as shown below in connection with FIG. 6. The sheets 28 and 34 are disposed on top of each other and are permanently connected to each other by any joining technique, as indicated by two rolls that form a joining station 38. An activation station 40 is provided in the supply direction downstream of the joining station 38, in which the elastically expandable properties of the elastically expandable material 36 are activated in that in some areas, as indicated in FIG. 6, the non-expandable carrier material 30 of the first sheet 28 is treated in an area 42 in such a fashion that it can no longer resist expansion. This can be achieved e.g. by overstretching in some areas by a "ring rolling" process, wherein the composite material formed by the first sheet 28 and the second sheet 34 is expanded in the area 42 by intermeshing roller surfaces, such that the carrier material 30 which is not expandable per se is overstretched and thereby plastically deformed (while the elastically expandable material 36 elastically follows the expansion). After passing the activation station 40, the pad side part sheet 22 is elastically expandable in the area 42 indicated in FIG. 6. The elastically expandable material 36 disposed in a lamellar fashion in the other areas outside of the area 42 cannot develop its elasticising effect, since the non-expandable carrier material 30 prevents substantial expansion of the pad side part sheet 22.

The pad side part sheet treated in this fashion is further supplied with the speed v1 towards a separating station 44 where longitudinal sections 46 are separated from the pad side part sheet 22 in a direction transverse to the supply direction and accelerated to a speed v2 by a schematically indicated acceleration roller 47 and supplied to the initially mentioned application station 24. These longitudinal sections 46 are limited in FIGS. 3 through 10 in each case by a separating line designated with reference numeral 48.

The bottom portion of FIG. 1 shows the supply and delivery of an endless pad main part sheet 50. The pad main part sheet carries an endless number of absorption cores 6 which are disposed one after the other and spaced apart. Also indicated is a covering layer 54. In the following, the absorption core 6 and the covering layer 54 are regarded as belonging to the pad main part sheet 50. The pad main part sheet is endlessly supplied towards the application station 24 at a speed v2. In the application station 24, the longitudinal sections 46 of the pad side part sheet 22 (FIG. 1) are applied to the pad main part sheet 50 in such a fashion that they are bridged in the area 52 between two absorption cores 6 or are disposed in this area. This is shown e.g. in the top view of FIGS. 8 and 9. The applied longitudinal sections 46 are undetachably connected, i.e. fixed, to the pad main part sheet 50 in the application station 24 or preferably substantially downstream thereof. Such a fixed area is e.g. designated with the reference numeral 56 in FIGS. 2, 8, and 9. The composite obtained in this fashion is further supplied towards a singling station 58 where a separating cut is performed substantially transversely to the supply direction which corresponds to the longitudinal direction 18 of the pad 2 to be produced, e.g. using a rotating knife drum or a punching tool. The separating cut is indicated in the figures with reference numeral 60. It is carried out in such a fashion that it extends in each case through the applied longitudinal section 46, dividing it into a first partial section 62 and a second partial section 64. The second partial section forms the pad side parts 10 provided in the rear hip area 14 and the first partial section 62 forms the pad side parts 8 provided in the front hip area 12.

Figure 3:
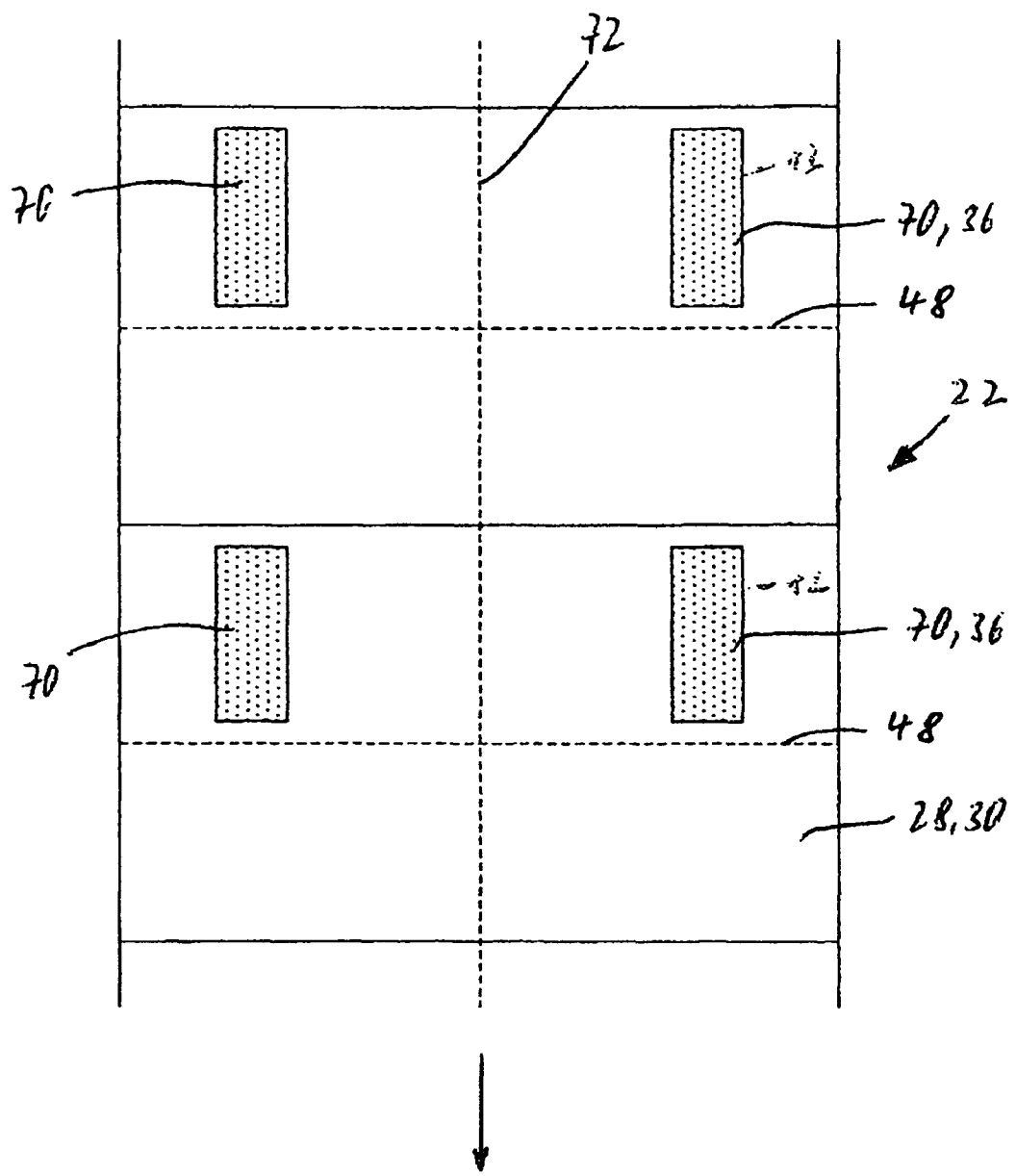
FIG. 3 shows a schematic top view of a pad side part sheet with indicated separating lines.

FIGS. 3 through 11 describe different inventive method variants:

In accordance with the method variant shown in FIG. 3, a pad side part sheet 22 is supplied in the direction of the arrow. It shows the first sheet 28 of carrier material 30 with lamellar sections 70 of elastically expandable material 36. In contrast to the schematic illustration of FIG. 1, the elastic material 36 is not continuously disposed onto the first sheet 28 in the supply direction (as shown in FIG. 6) but in spaced-apart sections 70. The carrier material 30 of the first sheet 28 is again substantially non-expandable. In order to render the area 42 of the lamellar sections 70 expandable, the non-elastic carrier material 30 in these areas must be treated as described above. In particular, the carrier material 30 may be locally overstretched at that location, or recesses could be provided at that location in the carrier material 30.

The pad side part sheet 22 is divided in the longitudinal direction into a left-hand and a right-hand sheet, as indicated by the central dashed line 72, which can then be joined to lateral areas of the pad main part sheet 4 as indicated in FIG. 2.

Figure 4:
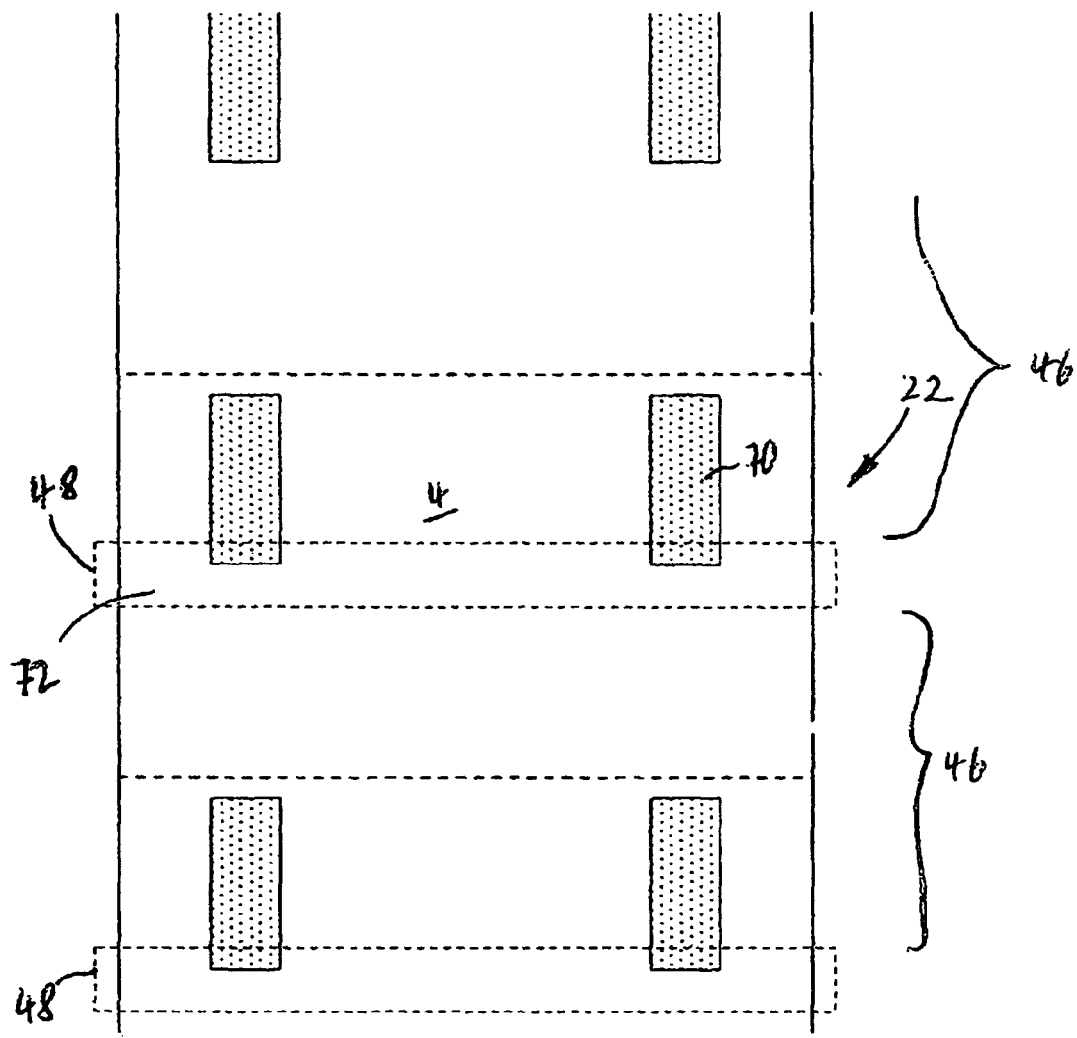
FIG. 4 shows a schematic top view of a pad side part sheet with indicated separating line shape (with off-cut)
Figure 5:
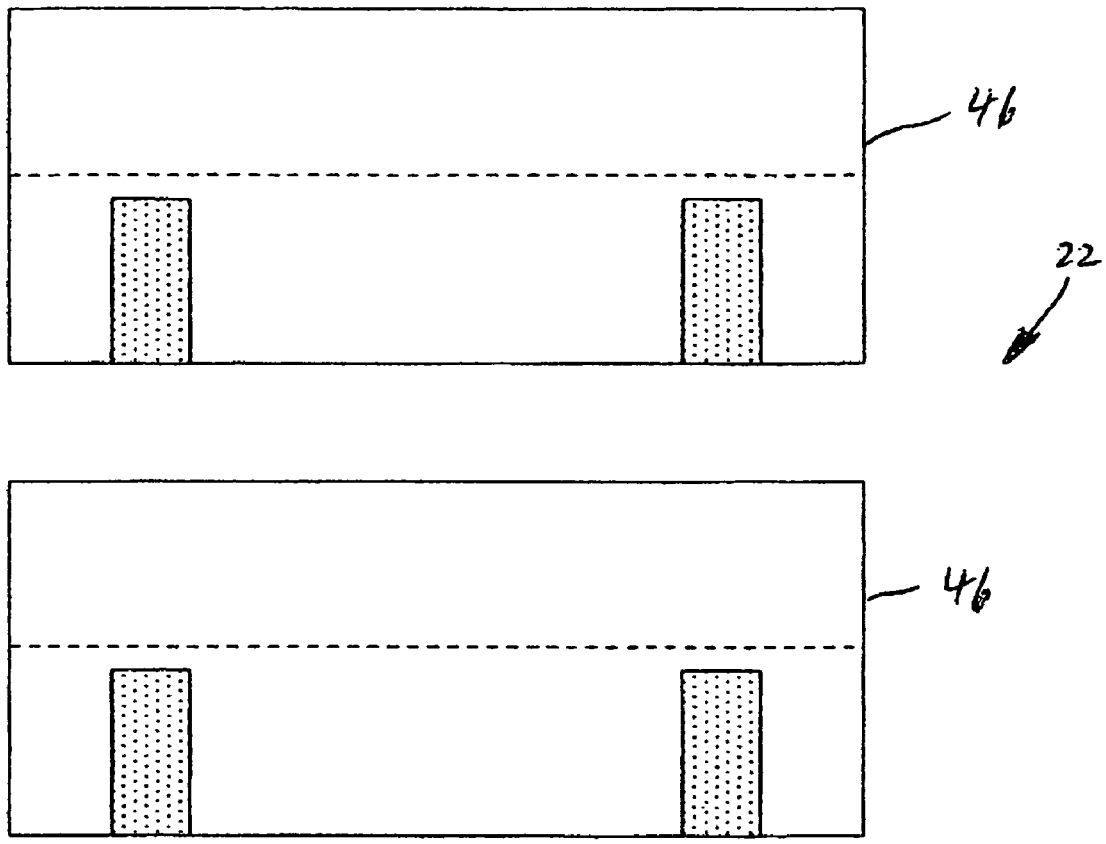
FIG. 5 shows a top view of separated longitudinal sections of the pad side part sheet of FIG. 4.

FIG. 4 shows the shape of a separating line 48 for forming longitudinal sections 46 in the separating station 44. The separating line 48 is guided in a rectangular fashion, such that a rectangular section 72 to be discarded is separated from the pad side part sheet 22. The separating line 48 is thereby guided in such a fashion that it includes the end of a respective lamellar section 70 of elastically expandable material 36. Positioning inaccuracies can thereby be compensated for and it is ensured that each lamellar section 70 extends flush with the rear hip edge of the pad 2 or the relevant pad main part 4. FIG. 5 shows the separated longitudinal sections 46 of the pad side part sheet 2. It must thereby be explicitly pointed out that it may also be advantageous to form one section to be discarded during separation when the pad 2 is singled in the singling station 58. In this fashion, the lamellar section 70 of elastically expandable material extends to the rear hip edge in accordance with the invention, at the same time ensuring that no elastic material extends into the front hip area 12 of the bordering pad 4 or the bordering pad main part 4. This is clearly shown in connection with FIG. 9 and explained below.

Figure 7:
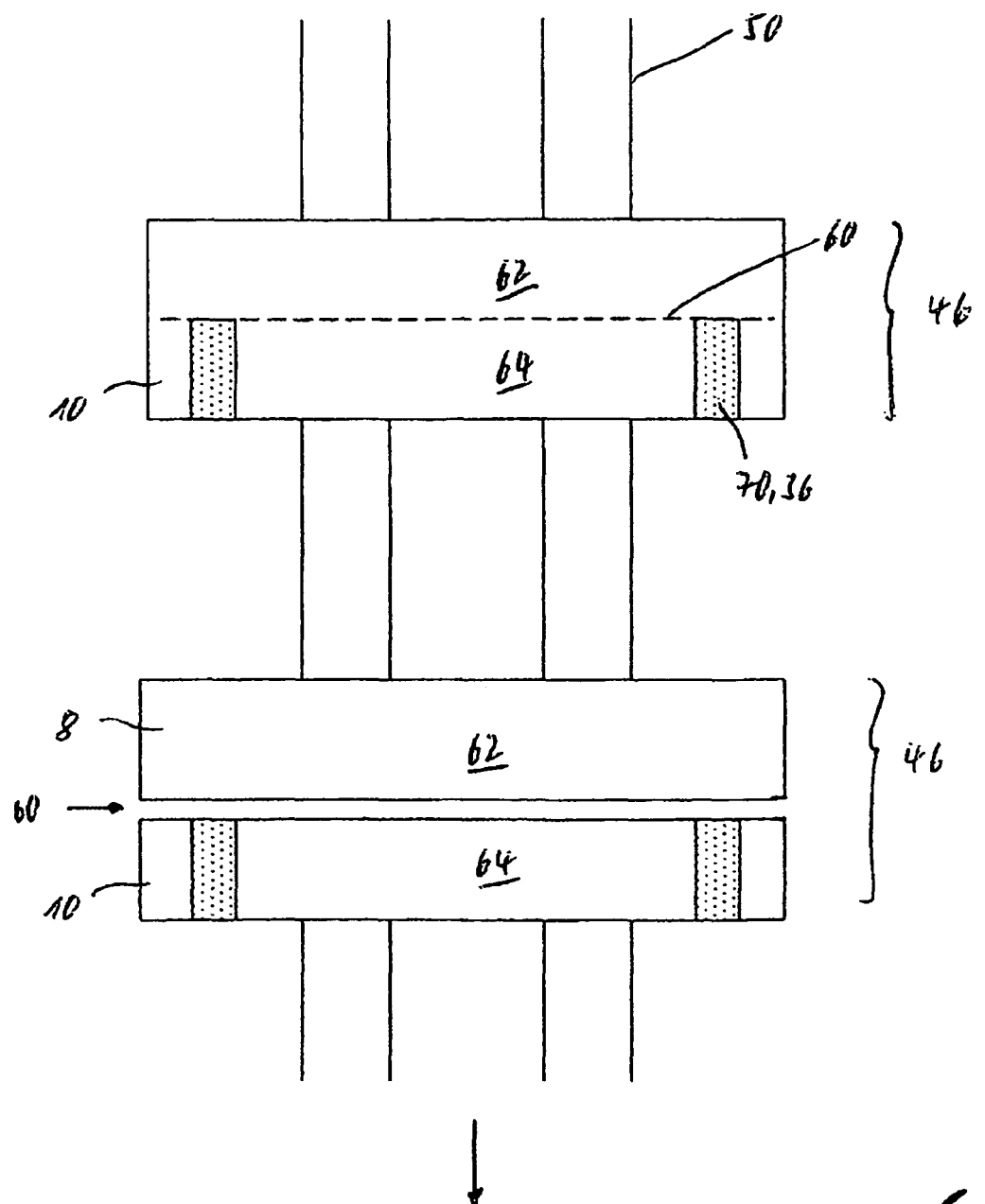
FIG. 7 shows a top view of a pad main part sheet with applied longitudinal sections of a pad side part sheet.

Instead of forming a section 72 to be discarded during separation of the longitudinal sections 46 from the pad side part sheet 22, separation along one single separating line 48 is also feasible as indicated in FIGS. 3 and 6. FIG. 7 schematically shows a pad main part sheet 50 onto which are disposed spaced-apart longitudinal sections 46 of a pad side part sheet 22, which are e.g. undetachably connected to the pad main part sheet 50 e.g. via ultrasound welding, glue etc. A separating cut 60 for singling the pads 2 is only indicated at the top of FIG. 7, while at the bottom of FIG. 7, the singling station 58 has already been passed and the separating cut 60 has been performed. A first partial section 62 is thereby formed which has no elastically expandable material 36, as well as a second partial section 64 having the lamellar section or area 70 of an elastically expandable material 36. The first partial section 62 forms front pad side parts 8 and the rear partial section 64 forms rear pad side parts 10. In the example of FIG. 7, the pad side part sheet 22 was not separated along its longitudinal direction into a left-hand and right-hand part, but a respectively formed longitudinal section 46 extends continuously in one piece in a transverse direction of the pad 2 over the width of the pad, i.e. continuously bridges the pad in the transverse direction (in contrast to the schematic view of FIG. 2).

Figure 11:
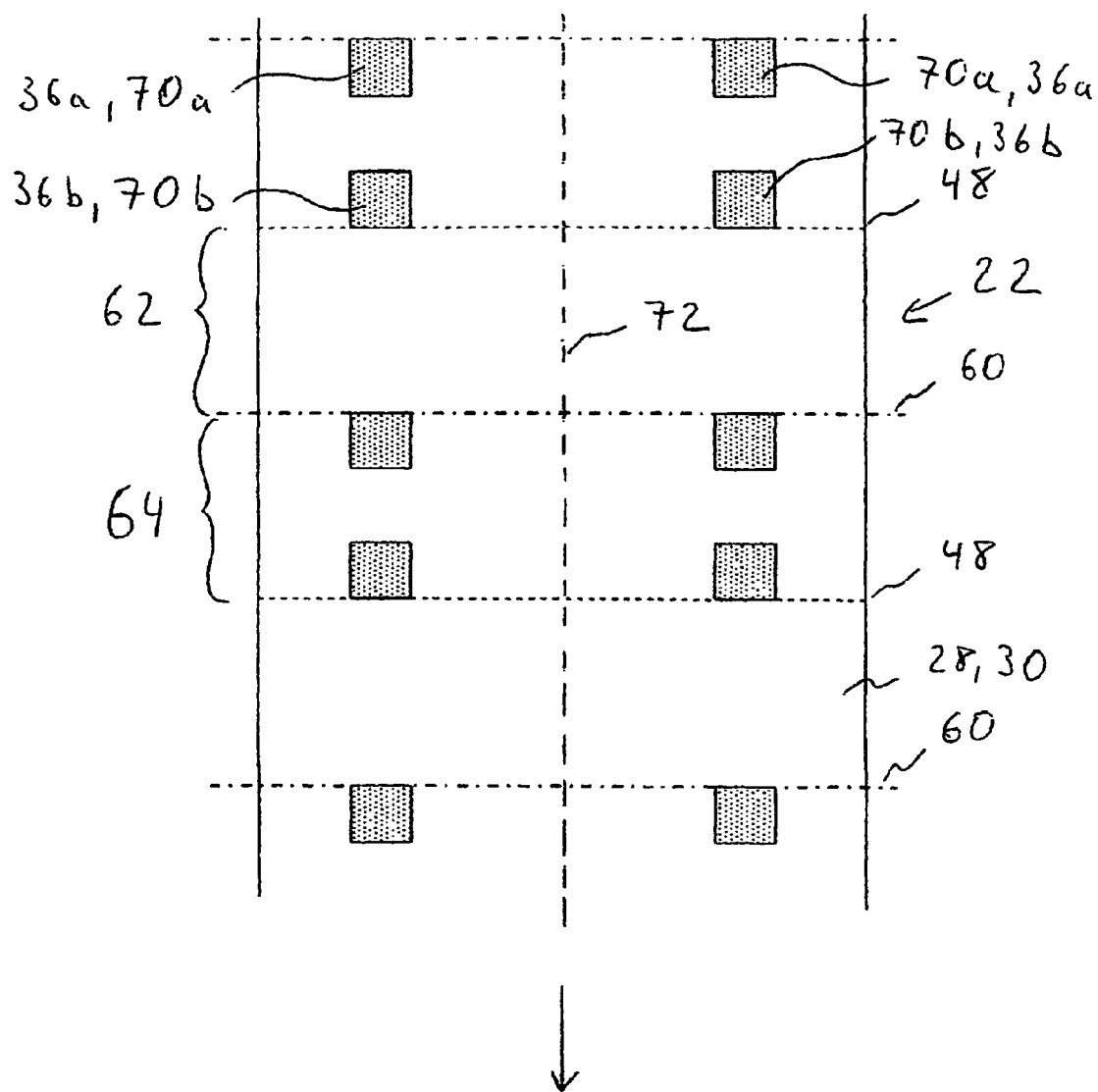
FIG. 11 shows a top view of a pad side part sheet according to a further inventive method variant.
Figure 12:
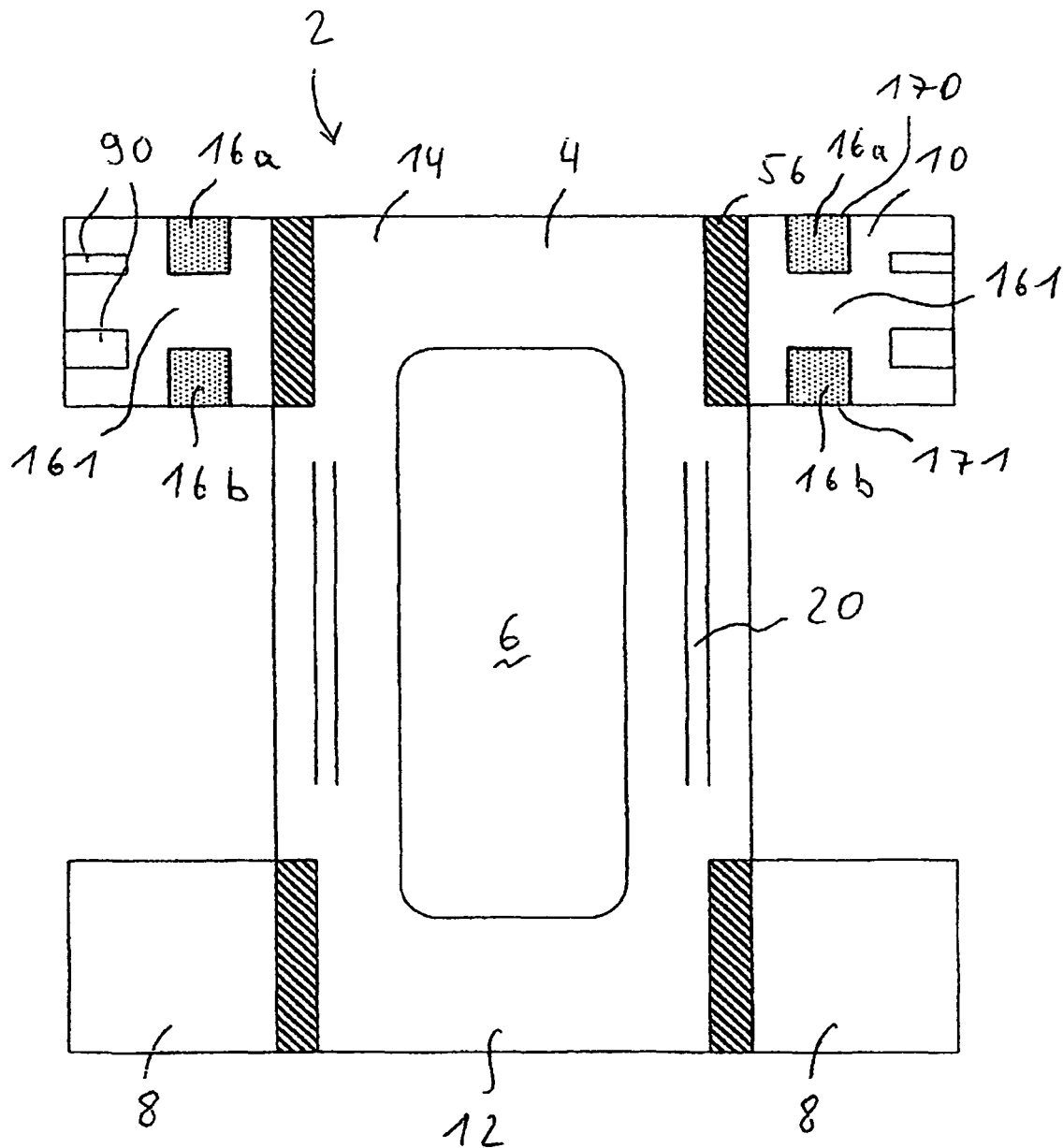
FIG. 12 shows a schematic top view of a disposable incontinence pad produced according to the inventive method, thereby providing a pad side part sheet produced according to FIG. 11.

In accordance with the method variant shown in FIG. 11, a pad side part sheet 22 is supplied in the direction of the arrow. The first sheet 28 of carrier material 30 is shown with lamellar sections 70a, 70b of elastically expandable material 36a, 36b. In contrast to the schematic display of FIG. 3, two lamellar sections 70a, 70b of elastically expandable material 36a, 36b are provided in each case in a respective second partial section 64 which forms a rear pad side part. A respective first partial section 62 which forms a front pad side part has no elastically expandable area. In consequence thereof, a respective rear pad side part 10 has a first expandable area 16a on or in the vicinity of an upper transverse edge 170 of the pad side part, and a second expandable area 16b on or in the vicinity of a lower transverse edge 171 as shown in FIG. 12. A substantially non-expandable area 161 remains between the expandable areas 16a, 16b. In this case, the rear pad side part has a higher expansibility at exactly that location where the greatest forces act during use according to experience e.g. during closing the disposable incontinence pad. This can prevent the pad side parts from being torn off the main part. The non-expandable area 161 also ensures a higher stability of the pad side part which is favorable for handling the disposable incontinence pad during use and also for production thereof in a fast running pad machine.

It is clear that the above-described elastically expandable areas, which are disposed discontinuously according to FIG. 11, may be provided merely by timed activation of elastic material which was previously continuously disposed in the supply direction in the above-described fashion.

Figure 8:
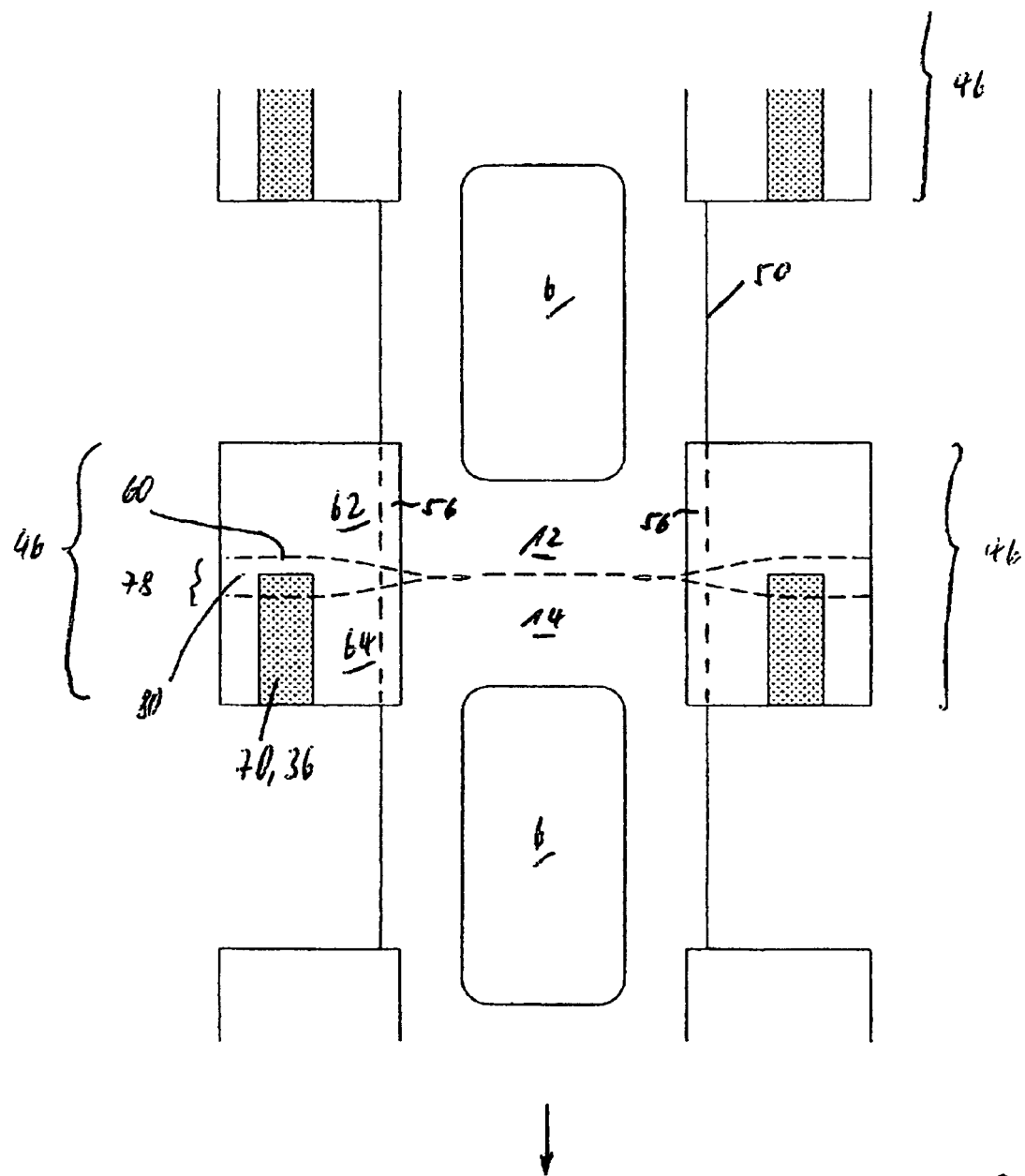
FIG. 8 shows a top view of a pad main part sheet with applied longitudinal sections of a pad side part sheet with indicated contour cut for singling.
Figure 9:
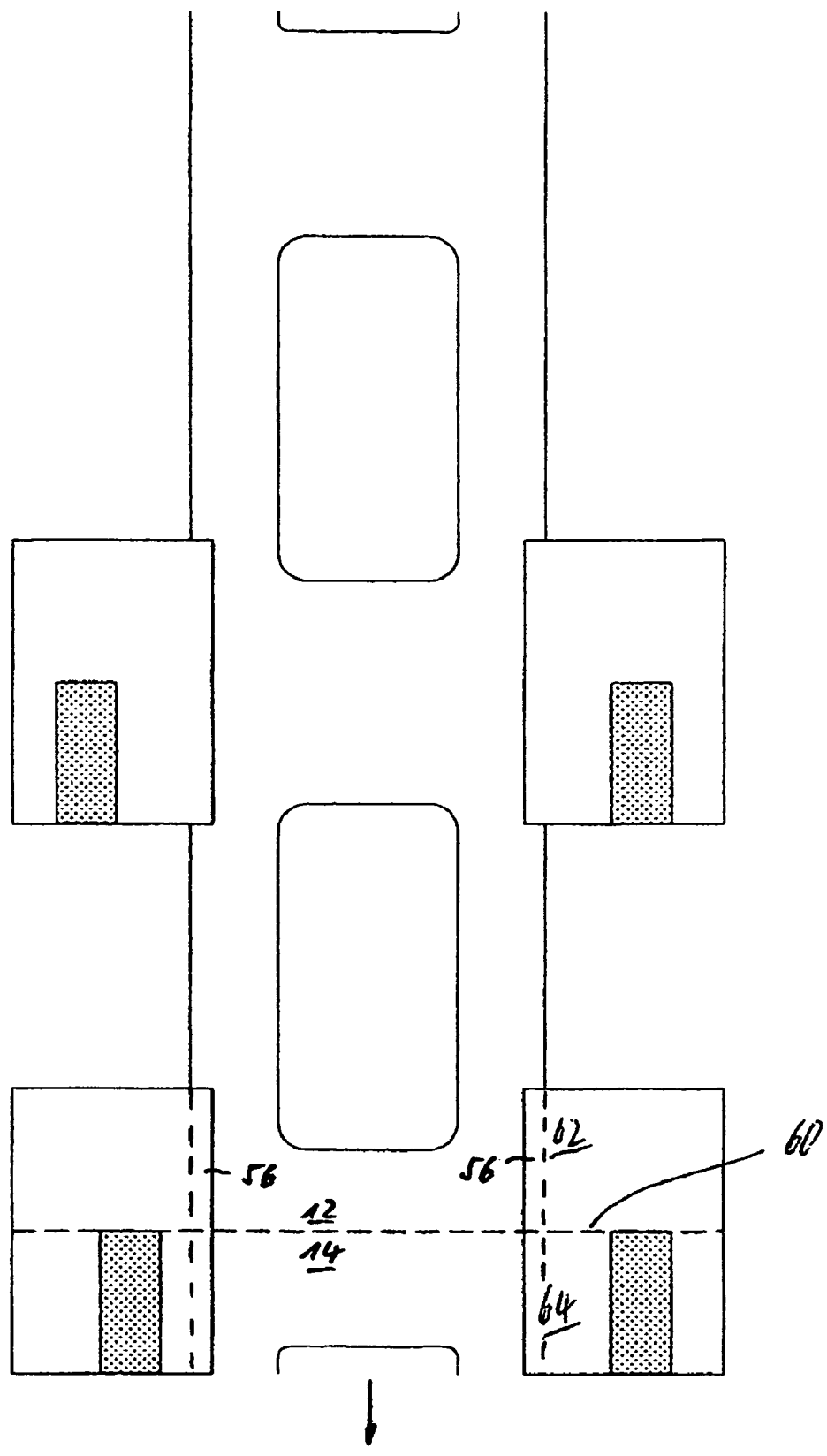
FIG. 9 shows a top view of a pad main part sheet with applied longitudinal sections with an indicated straight separating cut.

FIG. 8 shows another embodiment, wherein the pad side part sheet 22 was separated in the longitudinal direction into a left-hand and a right-hand part. This is advantageously, but not necessarily, effected upstream of the separating station 44 where the longitudinal sections 46 are formed. A left-hand and a right-hand longitudinal section 46 are correspondingly disposed onto the pad main part sheet 50 in the application station 24 and undetachably fixed. The shape of a separating cut 60 formed as a contour cut 78 is also indicated, which, however, produces a section 80 to be discarded. As explained already in connection with FIG. 4, this causes the lamellar area 70 of elastic material 36 to extend flush with the rear hip edge of the singled pad 2 and also prevents elastic material 36 from getting into the first partial section 62. The performance of one single, in particular, straight separating cut 60 is indicated in FIG. 9.

Figure 10:
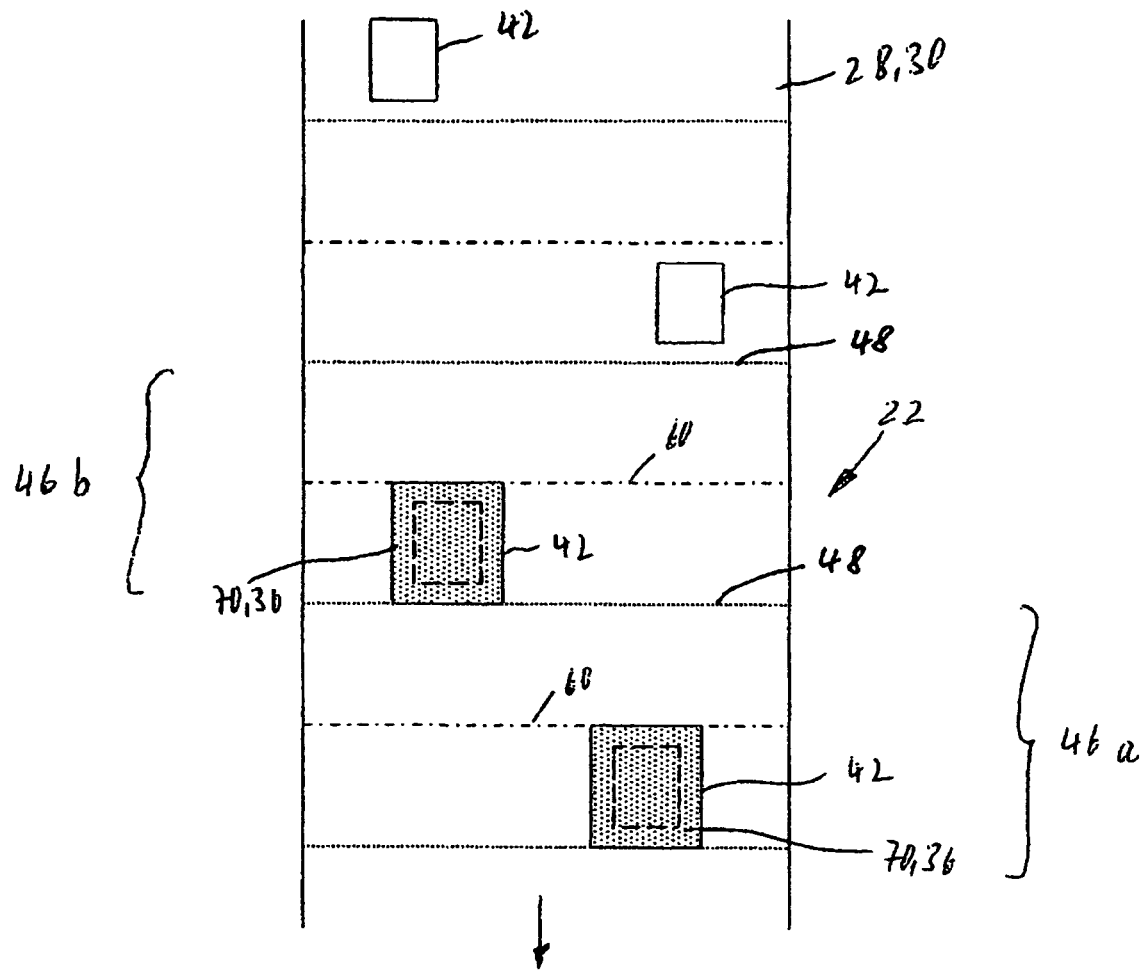
FIG. 10 shows a top view of a pad side part sheet according to a further inventive method variant.

FIG. 10 shows a further alternative inventive method variant, wherein the entire width of the available pad side part sheet 22 is used as a left-hand or right-hand pad side part in each case. It also indicates an area 42 in the first sheet 28 of carrier material 30 in which the non-elastic carrier material 30 is treated in such a fashion that it shows hardly any or no resistance at all to expansion. In particular, the area 42 could mark an area that is overstretched by "ring rolling". The respective area 42 is bridged by a section or area 70 of elastically expandable material 36, as shown below in the supply direction. The particularity of the method variant of FIG. 10 is that a right-hand and a left-hand side part are formed in an alternating fashion. This means that in the separating station 44, a first longitudinal section 46a and subsequent thereto, a second longitudinal section 46b are separated which are joined to the two sides of a pad main part sheet 50. A respective separating cut 60 for singling the pads is thereby not basically changed. According to this method variant, it is possible to realize a larger width of the pad side parts 8, 10, as mentioned above.

It is explicitly pointed out that the pad side parts 8, 10 may also be folded on top of themselves as disclosed and taught in DE202004006951.2. This folding or folding on top of itself is advantageously effected along a folding line that extends in the longitudinal direction upstream of the separating station 44 where the longitudinal sections 46 are formed. The sections folded on top of each other are preferably detachably fixed, in particular, by ultrasound weld points or by weak glue points, such that they are easy to unfold by hand.

We claim:

1. A method for producing a plurality of disposable incontinence pads having a pad main part and front and rear pad side parts joined thereto, the method comprising the steps of:
   a) supplying and delivering, in a first longitudinal direction, an endless pad main part sheet to an application station;
   b) preparing an endless pad side part sheet such that the endless pad side part sheet has a repetitive sequence of first and second regions which alternate in a longitudinal direction of the endless pad side part sheet, each first region having a first expandability and each second region having a second expandability, wherein said first expandability is less than said second expandability;
   c) directing the endless pad side part sheet towards the application station;
   d) separating, upstream of the application station and following step b), longitudinal sections of the pad side part sheet, each separated longitudinal section having a first longitudinal partial section containing one of the first regions having the first expandability and a second longitudinal partial section containing one of the second regions having the second expandability;
   e) supplying, following step d), the separated longitudinal sections to the application station;
   f) positioning the separated longitudinal sections on the pad main part sheet;
   g) permanently fixing the separated longitudinal sections of the pad side part sheet to the pad main part sheet; and
   h) singling the disposable incontinence pads by separating the pad main part sheet transversely to the longitudinal direction, wherein separation is performed through the separated longitudinal sections of the pad side part sheet such that the first partial section of a respective separated longitudinal section forms the front pad side part of a first disposable incontinence pad and the second partial section of the respective separated longitudinal section forms the rear pad side part of a directly bordering second disposable incontinence pad, the second partial section also comprising closure elements, wherein said rear pad side part has a greater expandability that said front pad side part.

2. The method of claim 1, wherein a respective pad main part has an absorption core that stores liquids.

3. The method of claim 1, wherein elastically expandable areas are provided on the pad side part sheet.

4. The method of claim 1, wherein at least two expandable areas are provided in the second partial section of the pad side part sheet, which are spaced apart in the longitudinal direction.

5. The method of claim 1, wherein first elastic elements are joined to the pad main part sheet, which extend in the first longitudinal direction.

6. The method of claim 5, wherein second elastic elements are joined to the pad main part sheet, which extend in the first longitudinal direction.

7. The method of claim 6, wherein the second elastic elements are formed by upright cuff elements.

8. The method of claim 1, wherein the pad side part sheet is supplied to the application station at a first speed v1 and the endless pad main part sheet is supplied to the application station at a second speed v2, wherein the first speed v1 is slower than the second speed v2.

9. The method of claim 8, wherein the second speed v2 is faster than the first speed v1 by at least 40%, at least 70%, at least 90% or at most 200%.

10. The method of claim 1, wherein elastic areas of the pad side part sheet are formed by disposing elastic material onto a carrier material and overstretching the carrier material in some areas.

11. The method of claim 1, wherein elastic material of the pad side part sheet is formed by a lamellar elastic material that extends continuously in the longitudinal direction of the pad side part sheet and is activated only in sections in the longitudinal direction.

12. The method of claim 10, wherein the elastic material is disposed like a sandwich between a first and a second carrier material.

13. The method of claim 1, wherein a longitudinal section of the pad side part sheet is formed continuously in one piece in a transverse direction of the pad such that it continuously bridges a respective front or rear hip area of the pad main part.

14. The method of claim 1, wherein, in a longitudinal direction of the pad side part sheet, one longitudinal section is provided for forming a right-hand pad side part and, subsequent thereto, a longitudinal section is provided for forming a left-hand pad side part.

15. The method of claim 1, wherein a section to be discarded is formed during singling of the disposable incontinence pads or during separation of the longitudinal sections.

16. The method of claim 1, wherein a contour cut is performed during singling.

17. The method of claim 1, wherein the rear pad side part has an expansibility of at least 20%, at least 25%, or of at least 30% under action of a force of 45N.

18. The method of claim 1, wherein the front pad side part has an expansibility of at most 15%, at most 10%, or of at most 8% under action of a force of 45N.

19. The method of claim 1, wherein front pad side parts are substantially non-expandable.

20. The method of claim 1, wherein pad side parts are folded about at least one or about two folding lines that extend in the longitudinal direction.

21. The method of claim 1, wherein the pad side parts are folded on top of each other and are detachably fixed in that configuration.

22. The method of claim 1, wherein singled disposable incontinence pads are folded about at least one or about two folding lines that extend transversely to the longitudinal direction.

* * * * *